United States Patent
Macduff

(10) Patent No.: US 9,375,319 B2
(45) Date of Patent: Jun. 28, 2016

(54) BIO-MECHANICAL PROSTHETIC THUMB

(71) Applicant: RCM Enterprise, L.L.C., Tumwater, WA (US)

(72) Inventor: Charles Colin Macduff, Olympia, WA (US)

(73) Assignee: RCM Enterprise, LLC, Tumwater, WA (US)

(*) Notice: Subject to any disclaimer, the term of this patent is extended or adjusted under 35 U.S.C. 154(b) by 0 days.

(21) Appl. No.: 14/230,119

(22) Filed: Mar. 31, 2014

(65) Prior Publication Data

US 2014/0303750 A1 Oct. 9, 2014

Related U.S. Application Data

(60) Provisional application No. 61/806,778, filed on Mar. 29, 2013.

(51) Int. Cl.
| | |
|---|---|
| *A61F 2/54* | (2006.01) |
| *A61F 2/42* | (2006.01) |
| *A61F 2/58* | (2006.01) |
| *A61F 2/78* | (2006.01) |
| *A61F 5/01* | (2006.01) |
| *A61F 2/50* | (2006.01) |

(52) U.S. Cl.
CPC .............. *A61F 2/4241* (2013.01); *A61F 2/586* (2013.01); *A61F 5/013* (2013.01); *A61F 2002/5038* (2013.01); *A61F 2002/587* (2013.01); *A61F 2002/7856* (2013.01); *A61F 2002/7862* (2013.01)

(58) Field of Classification Search
CPC .... A61F 2/586; A61F 2002/587; A61F 5/013
USPC ........................................... 623/63–64; 602/22
See application file for complete search history.

(56) References Cited

U.S. PATENT DOCUMENTS 319,776 A 6/1885 Bashore
984,179 A 2/1911 Aydt
(Continued)

FOREIGN PATENT DOCUMENTS

| GB | 110333 | 10/1917 | | |
|---|---|---|---|---|
| GB | 2488365 A | * | 8/2012 | ............... A61F 2/74 |
| JP | 2002-345861 A | * | 12/2002 | ............... A61F 2/56 |

OTHER PUBLICATIONS

Leow, M., et al. "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.
(Continued)

*Primary Examiner* — David H Willse
(74) *Attorney, Agent, or Firm* — Sheridan Law, LLC; James A. Sheridan

(57) ABSTRACT

There is disclosed a prosthetic thumb assembly. In an embodiment, the assembly includes a distal phalanges. The assembly includes a proximal phalanges having an operable connection with the distal phalanges. The assembly includes a thumb strap ring having an operable connection with the distal phalanges. The assembly includes a proximal phalanges yoke having an operable connection with the thumb strap ring. The assembly includes an anchoring portion having an operable connection with the thumb strap ring. Other embodiments are also disclosed.

12 Claims, 20 Drawing Sheets

(56) References Cited

U.S. PATENT DOCUMENTS

| | | | |
|---|---|---|---|
| 2,706,296 A | 4/1955 | Fletcher | |
| 2,867,819 A | 1/1959 | George | |
| 3,483,718 A | 12/1969 | Lodrini | |
| 3,707,963 A * | 1/1973 | Keropian | 602/21 |
| 4,997,433 A | 3/1991 | Goble et al. | |
| 5,062,855 A | 11/1991 | Rincoe | |
| 5,941,914 A | 8/1999 | Jacobsen et al. | |
| 6,908,489 B2 | 6/2005 | Didrick | |
| 8,337,568 B2 | 12/2012 | Macduff | |
| 2004/0054424 A1 | 3/2004 | Matsuda | |
| 2005/0043822 A1 | 2/2005 | Didrick | |
| 2006/0224249 A1 | 10/2006 | Winfrey | |
| 2010/0082103 A1 | 4/2010 | Blunn et al. | |
| 2011/0144770 A1 | 6/2011 | Moyer et al. | |
| 2012/0330432 A1 | 12/2012 | Fong | |
| 2013/0268094 A1 | 10/2013 | Van Wiemeersch | |
| 2014/0371897 A1 | 12/2014 | Lin et al. | |

OTHER PUBLICATIONS

Cabibihan, J. "Patient-Specific Prosthetic Fingers by Remote Collaboration—a Case Study", PLoS One, May 2011, vol. 6, No. 5.
International Search Report and Written Opinion for PCT/US16/16215, Apr. 22, 2016, 8 pp.

* cited by examiner

BIO-MECHANICAL PROSTHETIC THUMB

REFERENCE TO PENDING PRIOR PATENT APPLICATION

This application claims the benefit under 35 U.S.C. 119(e) of U.S. Provisional Patent Application No. 61/806,778, filed Mar. 29, 2013 by Charles Colin Macduff for "Bio-Mechanical Prosthetic Thumb (BPT), formally known as the Mechanical Finger Ring (MFR)," which patent application is hereby incorporated herein by reference.

BACKGROUND

If a person loses a thumb, thumb segment, or thumb tip, the result is impaired performance of the hand. Having an amputated thumb or thumb tip inhibits an amputee from performing some of the most basic tasks. For example, with a lost thumb or thumb tip, the task of typing on a computer or simply dialing on a phone becomes significantly difficult. These types of tasks require the actions with precision that only fingers are able to offer. Not only do fingers allow people to perform precise actions, but fingers also provide people with a increased ability to handle items. While holding an item in one hand, the weight of the item is dispersed through all of a user's fingers. By simply varying the force used by each finger on the holder's hands, the holder is able to manipulate the item in a myriad of ways. However, if the holder is missing a single finger, the amount of precision for the manipulation and the number of ways the holder can manipulate the item is decreased.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a prosthetic thumb assembly, comprising a distal phalanges; a proximal phalanges having an operable connection with the distal phalanges; a thumb strap ring having an operable connection with the distal phalanges; a proximal phalanges yoke having an operable connection with the thumb strap ring; and an anchoring portion having an operable connection with the thumb strap ring.

In another embodiment, there is provided a prosthetic full finger assembly, comprising a distal phalanges having an operable connection at a proximal end thereof; a metacarpal back plate having an operable connection adjacent a distal end thereof and an anchor adjacent a proximal end thereof; and articulation components configured between the metacarpal back plate and the distal phalanges; wherein the metacarpal back plate is configurable for placement on a back portion of a hand, when a metacarpal joint in the hand is bent the articulation components are articulated to articulate the distal phalanges.

Other embodiments are also disclosed.

The present invention relates generally to a prosthetic device, more specifically, to a prosthetic device designed for partial thumb or thumb-tip amputees.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
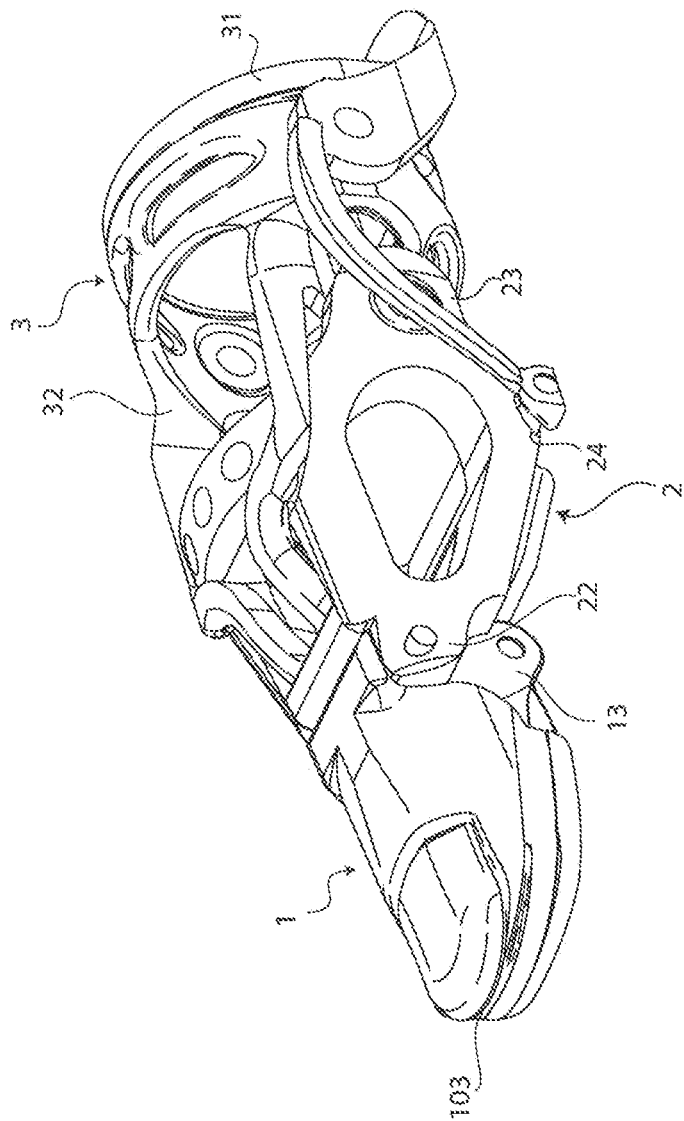
FIG. 1 is a perspective view of a prosthetic partial finger device.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The present invention is a prosthetic finger that can be fitted for a user with an amputated finger, fingertip, or finger segment. The prosthetic finger is a mechanical finger that is able to mimic the motions and functionalities of a real finger. The mechanical prosthetic finger comprises of three major components including a distal phalanges 1, a middle phalanges 2, and a proximal phalanges ring 3. A plurality of rods 8 and a series of hinges are used to secure the distal phalanges 1, the middle phalanges 2, and the proximal phalanges ring 3 together. The distal phalanges 1 is the tip segment of the prosthetic finger. The middle phalanges 2 is the middle segment of the prosthetic finger. The proximal phalanges ring 3 is the base of the prosthetic finger that anchors the entire prosthetic finger to the user's residual finger. As the level of amputation differs among each user, the present invention can be modified to be custom fit for each user. For example, users who have an amputated finger tip will be custom fitted with a prosthetic finger, where the middle phalanges 2 and the proximal phalanges ring 3 are frames that fit and mount to the user's residual finger. To provide the prosthetic finger with grip and a softer touch, the present invention additionally comprises a distal pad platform 4, a distal pad 5, a middle pad platform 6, and a middle pad 7. The distal pad 5 and the middle pad 7 are made from a soft texture that mimics the texture of a real finger. In the preferred embodiment of the present invention, to additionally contribute to the realistic aspect of the prosthetic finger, the present invention further comprises of an articulation cable 9 and a touch screen mechanism 10. The articulation cable 9 further provides the prosthetic finger with realistic curling motions. The touch screen mechanism 10 allows the user to use the prosthetic finger to operate touch screens. Although some touch screens, such as resistive touch screens, only require pressure for sensing the touch, other touch screens use the body's natural current to sense touch. These touch screens that require the user's natural body current are called capacitive touch screens. The touch screen mechanism 10 allows the user to conduct their own body current and direct it towards the tip of the prosthetic finger.

Figure 2:
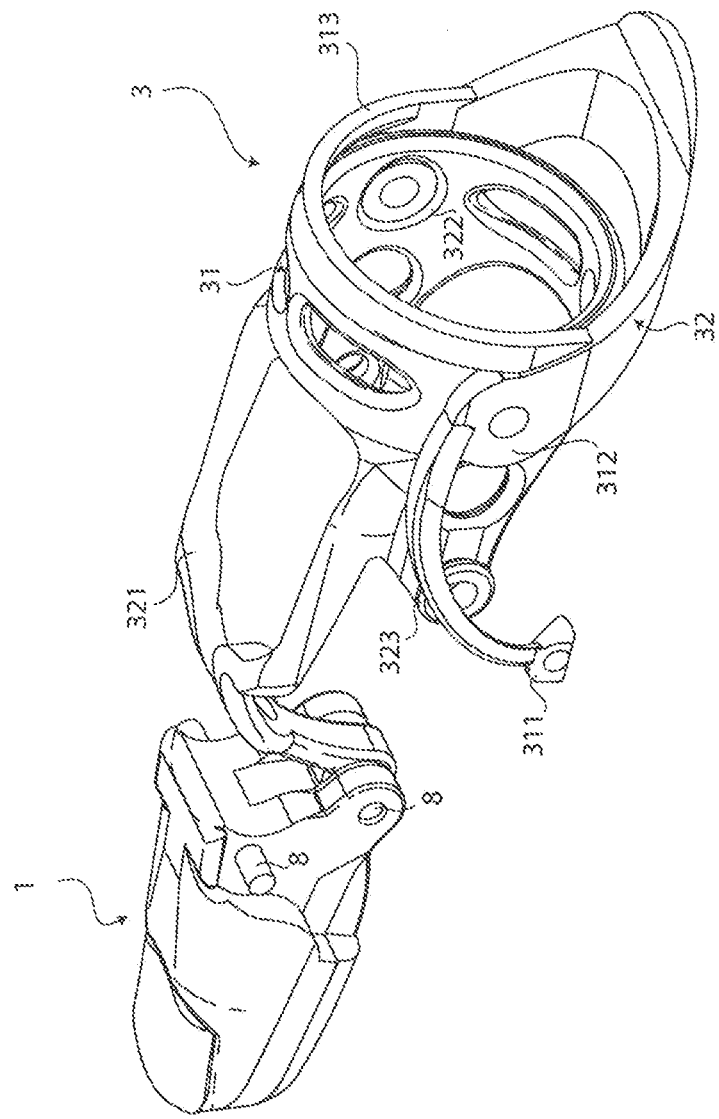
FIG. 2 is a view of the present invention without the middle phalanges showing the connection of the extended wishbone hinge to the pair of proximal pulling hinges.
Figure 3:
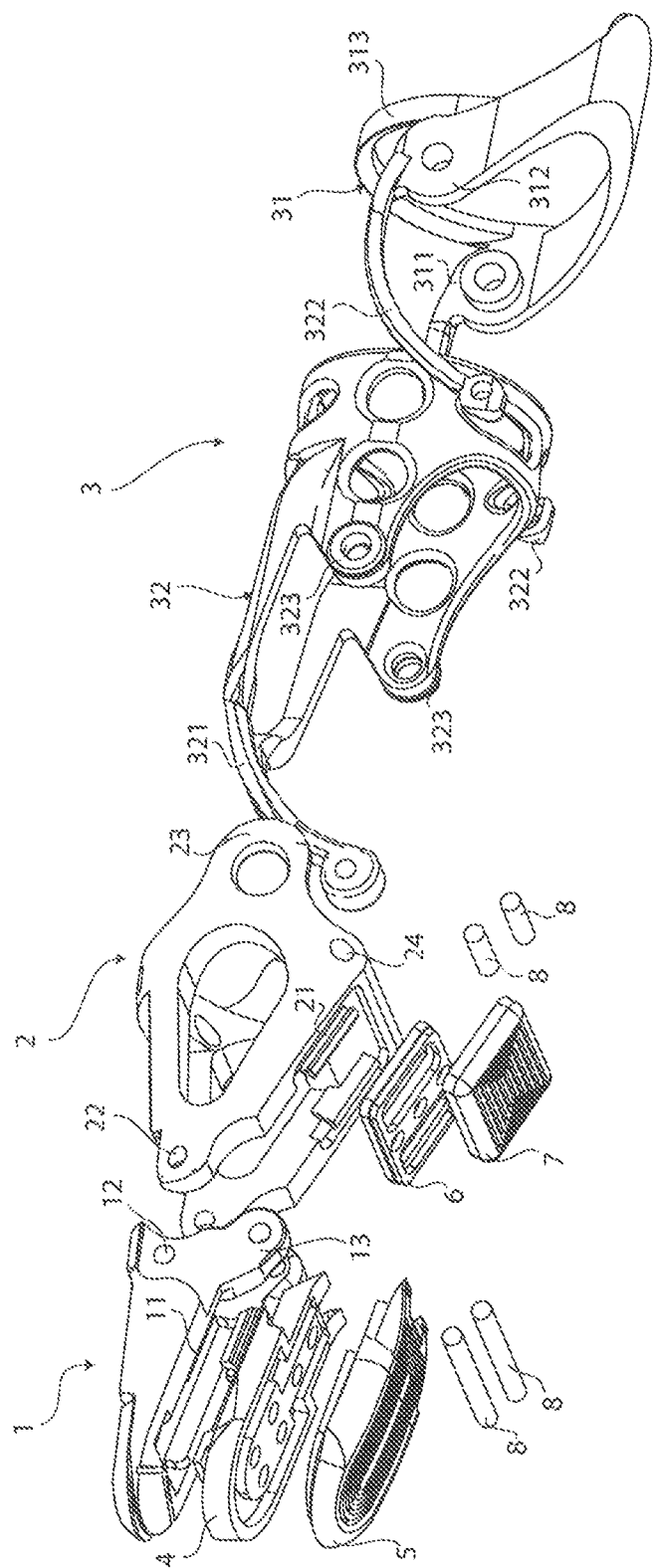
FIG. 3 is an exploded view of the present invention.

In reference to FIG. 1-3, the distal phalanges 1 comprises a distal platform fastener 11, a middle phalanges joint channel 12, and a pair of proximal pulling hinges. The distal pad 5 and the distal pad platform 4 are secured to the distal phalanges 1. The distal pad 5 is engaged and adhered to the distal pad platform 4 by a RTV silicone adhesive. The use of such an adhesive is important when using a silicone material for the distal pad 5 due to its high temperature material. The distal pad 5 is made from a soft material, such as silicone, to mimic the flesh of a real finger pad. The distal pad 5 is attached to the distal phalanges 1 by means of the distal pad platform 4. The distal pad platform 4 is secured to the distal platform fastener 11 of the distal phalanges 1. In the preferred embodiment of the present invention, the distal platform fastener 11 is a distal platform latch and the distal pad platform 4 comprises of a corresponding latch hole. However, in other embodiments of the present invention, the distal platform fastener 11 can simply be an adhesive. The distal platform fastener 11 is positioned on a lower distal surface of the distal phalanges 1. In comparison to a real finger, the positioning of the distal platform fastener 11 allows the distal pad 5 to be positioned where the finger pads of a real finger would be. The distal phalanges 1, the distal pad 5, and the distal pad platform 4 combine together to be shaped like a real finger tip. On the rear end of the distal phalanges 1 is the middle phalanges joint channel 12. The middle phalanges joint channel 12 is a hole that laterally traverses through the distal phalanges 1. The middle phalanges joint channel 12 provides a pivot point for the connection of the middle phalanges 2. The pair of proximal pulling hinges 13 is a pair of hinge channels that downwardly extends at an angle from the rear of the distal phalanges 1. The pair of proximal pulling hinges 13 are positioned adjacent to the middle phalanges joint channel 12. The pair of proximal pulling hinges 13 provides a pulling point for the proximal phalanges ring 3 to pull on to mimic the curling motion of a real finger.

In reference to FIG. 1-3, the middle phalanges 2 comprises a middle platform fastener 21, a pair of distal joint hinges 22, a pair of proximal joint hinges 23, and a pair of spring hinge ports 24. For a finger amputee with a missing finger tip, the middle phalanges 2 is a frame that wraps around the intermediate phalanges of the user's residual finger. The middle pad 7 and the middle pad platform 6 are secured to the middle phalanges 2. The middle pad 7 is engaged and adhered to the middle pad platform 6 by a RTV silicone adhesive. Similar to the distal pad 5, the middle pad 7 is made from a soft material, such as silicone. The middle pad 7 is attached to the middle phalanges 2 by means of the middle pad platform 6. The middle pad platform 6 is secured to the middle platform fastener 21 of the middle phalanges 2. In the preferred embodiment of the present invention, similar to the distal platform fastener 11, the middle platform fastener 21 is a middle platform latch and the middle pad platform 6 comprises of a corresponding latch hole. In other embodiments, the middle platform fastener 21 can be an adhesive. The middle platform fastener 21 is positioned on a lower middle surface of the middle phalanges 2. Similar to the distal phalanges 1, the positioning of the middle platform fastener allows the middle pad 7 to be positioned where the finger pads of the intermediate phalanges of a real finger would be. The middle phalanges 2, the middle pad 7, and the middle pad platform 6 combine together to be shaped like a real intermediate phalanges. The pair of distal joint hinges 22 is forwardly extended from the middle phalanges 2 in parallel relationship to each other. The pair of proximal joint hinges 23 is extended from the middle phalanges 2 in an opposite direction of the pair of distal joint hinges 22. As a result, the pair of distal joint hinges 22 and the pair of proximal joint hinges 23 are positioned on opposite ends of the middle phalanges 2. The middle phalanges 2 is able to jointly connect the distal phalanges 1 to the proximal phalanges ring 3 together by means of the pair of distal joint hinges 22 and the pair of proximal joint hinges 23.

In reference to FIG. 1-3, the proximal phalanges ring 3 is a two-part component comprising a proximal phalanges yoke 31 and a proximal phalanges frame 32. The proximal phalanges frame 32 is the body of the proximal phalanges ring 3 that anchors itself onto the user's finger. The proximal phalanges yoke 31 is the brace of the proximal phalanges ring 3 that provides support in the motion provided by the present invention. The proximal phalanges yoke 31 further comprises a pair of extending spring hinges 311, a pair of frame joint hinges 312, and a finger base brace 313. The proximal phalanges frame 32 comprises an extended wishbone hinge 321, a pair of posterior yoke joint hinges, and a pair of anterior phalanges joint hinges 323. The finger base brace 313 is a circular frame that is the body of the proximal phalanges yoke 31. The finger base brace 313 is shaped to fit the base of the user's residual finger. The pair of frame joint hinges 312 is extended from the finger base brace 313. The pair of extending spring hinges 311 is a flat spring hinge that extends from the pair of frame joint hinges 312. The extended wishbone hinge 321 is shaped like a wishbone and is forwardly extending from the proximal phalanges frame 32. The pair of anterior phalanges joint hinges 323 extend from the proximal phalanges frame 32 adjacent to the extended wishbone hinge 321. The pair of posterior yoke joint holes 322 are holes that laterally traverse through the proximal phalanges. The proximal phalanges yoke 31 is jointly connected to the proximal phalanges frame 32. The pair of frame joint hinges 312 are aligned with and engaged to the pair of posterior yoke joint holes 322. The pair of frame joint hinges are able to jointly connect to the pair of posterior yoke joint holes 322 by means of a yoke stud. The yoke stud is inwardly protruding from each of the frame joint hinges. The proximal phalanges yoke 31 is then aligned with and jointly secured to the pair of posterior yoke joint holes 322.

In reference to FIG. 1-3, the distal phalanges 1 is connected to the middle phalanges 2. The proximal phalanges ring 3 is connected to the middle phalanges 2 opposite of the distal phalanges 1. The plurality of rods 8 is traversed through the pair of distal joint hinges 22, the middle phalanges joint channel 12, the pair of proximal joint hinges 23, the pair of extending spring hinges 311, the extended wishbone hinge 321, and the pair of proximal pulling hinges for the assembly. The plurality of rods 8 consists of a first rod, a second rod, and a third rod. The pair of distal joint hinges 22 is aligned and secured to the middle phalanges joint channel 12 by the first rod. The pair of spring hinge ports 24 is aligned and secured to the pair of extending spring hinges 311 by the second rod. The extended wishbone hinge 321 is aligned and secured to the pair of proximal pulling hinges 13 by the third rod. The extended wishbone is extended over and traversed through the middle phalanges 2 for its connection to the pair of proximal pulling hinges 13. Each of the anterior phalanges joint hinges 323 comprises a middle stud. The middle stud is an outwardly protruding stud from each anterior phalanges joint hinge 323. The pair of anterior phalanges joint hinges 323 are aligned and jointly secured to the pair of proximal joint hinges 23 by the middle stud. All of the joint connections described provide the prosthetic finger with the ability to curl and move like a real finger.

Figure 4:
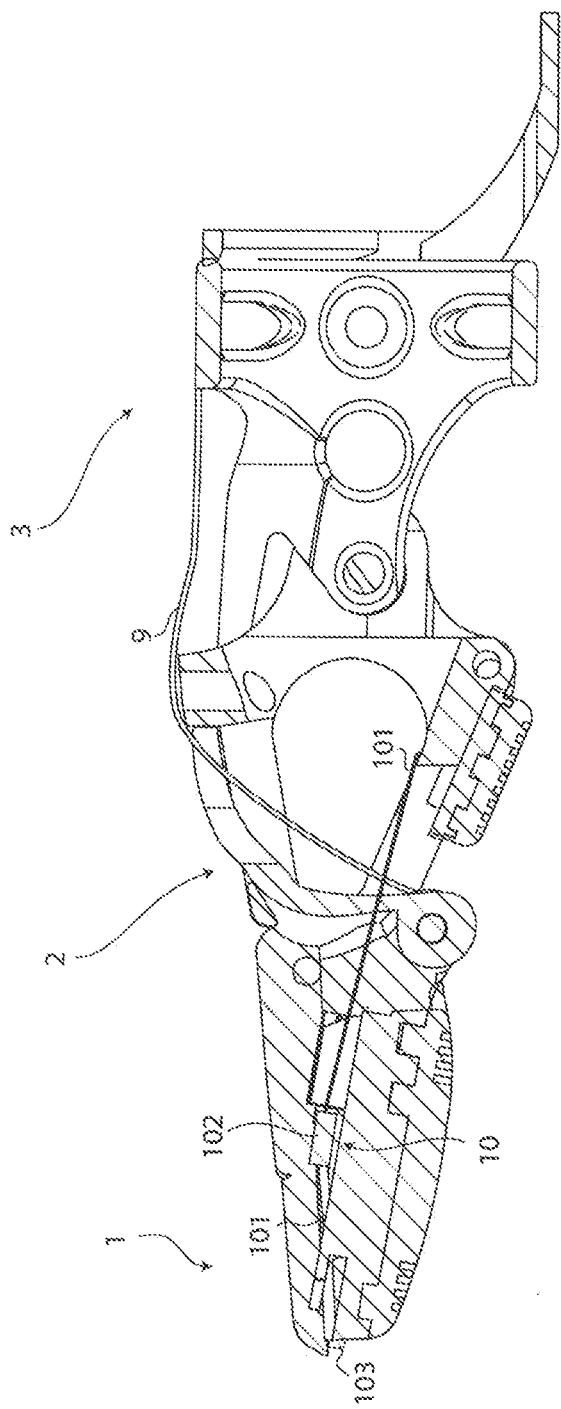
FIG. 4 is a cross sectional view of the present invention showing the articulation cable and the touch screen mechanism.
Figure 5:
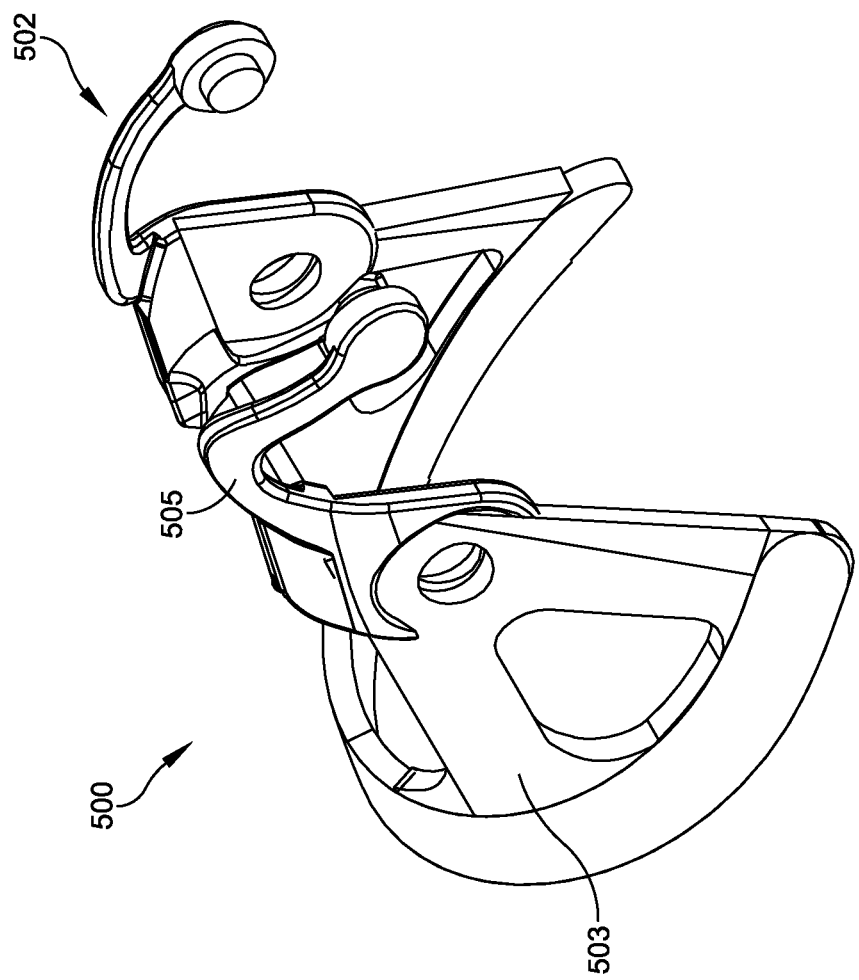
FIG. 5 is a perspective view of a portion of an embodiment of a prosthetic thumb assembly.
Figure 6:
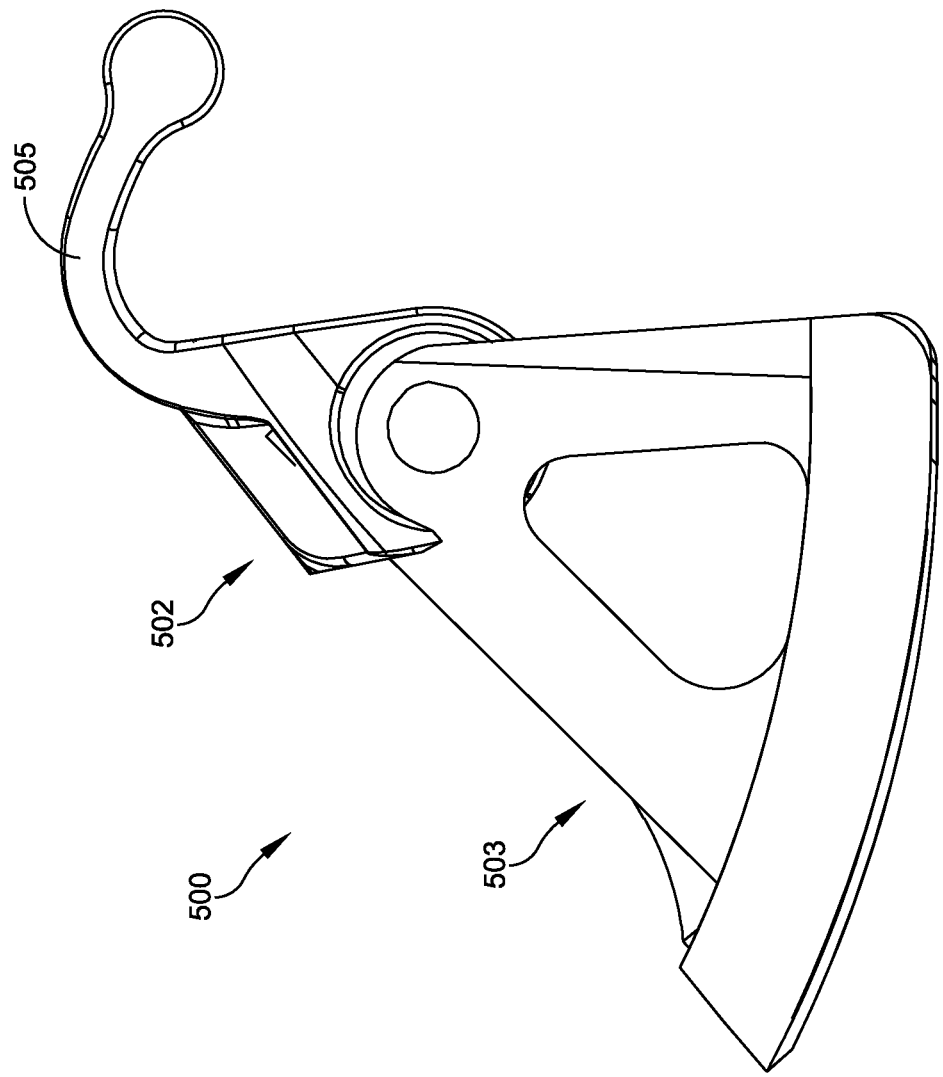
FIG. 6 is a front view of the portion of the prosthetic thumb assembly of FIG. 5.
Figure 7:
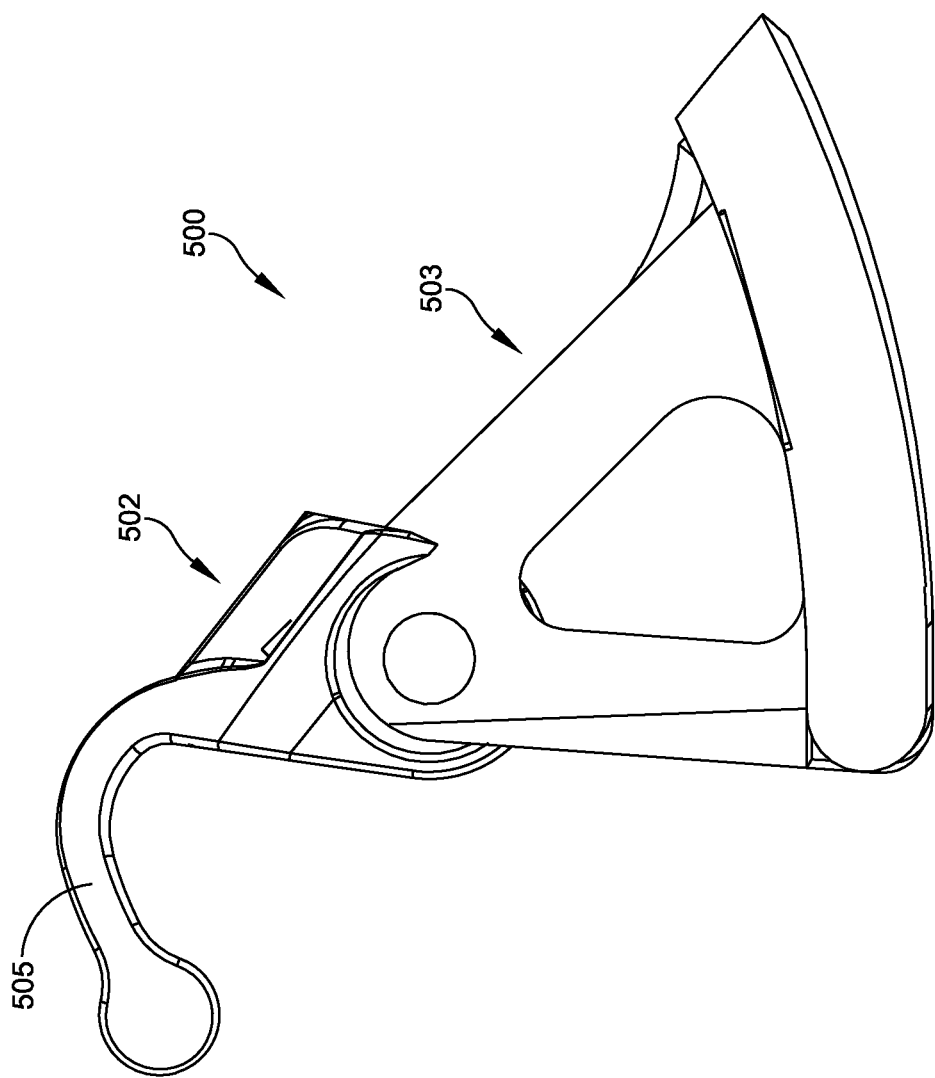
FIG. 7 is a rear view of the portion of the prosthetic thumb assembly of FIG. 5.
Figure 8:
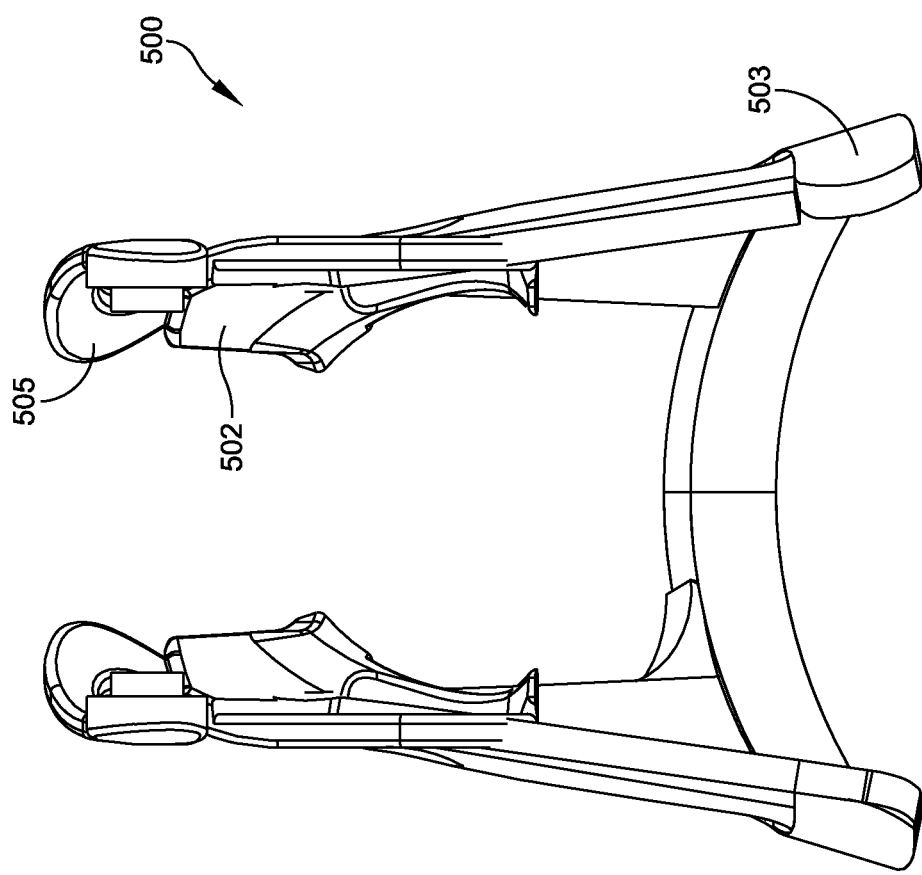
FIG. 8 is a right side view of the portion of the prosthetic thumb assembly of FIG. 5.
Figure 9:
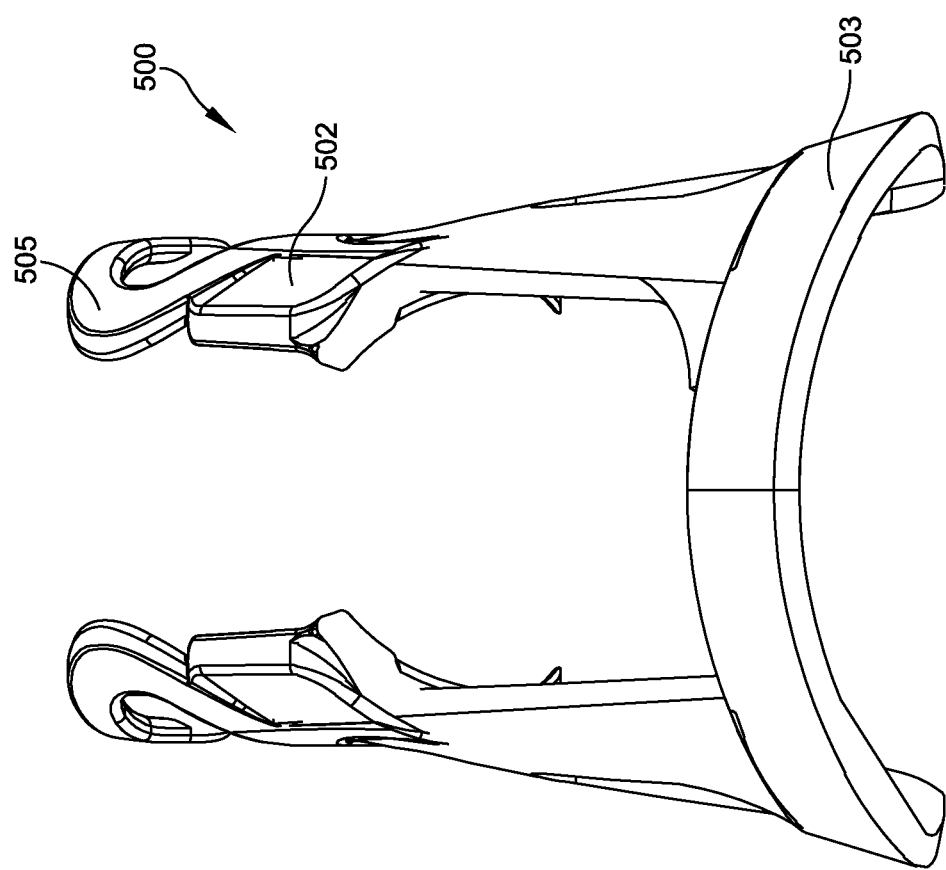
FIG. 9 is a left side view of the portion of the prosthetic thumb assembly of FIG. 5.
Figure 10:
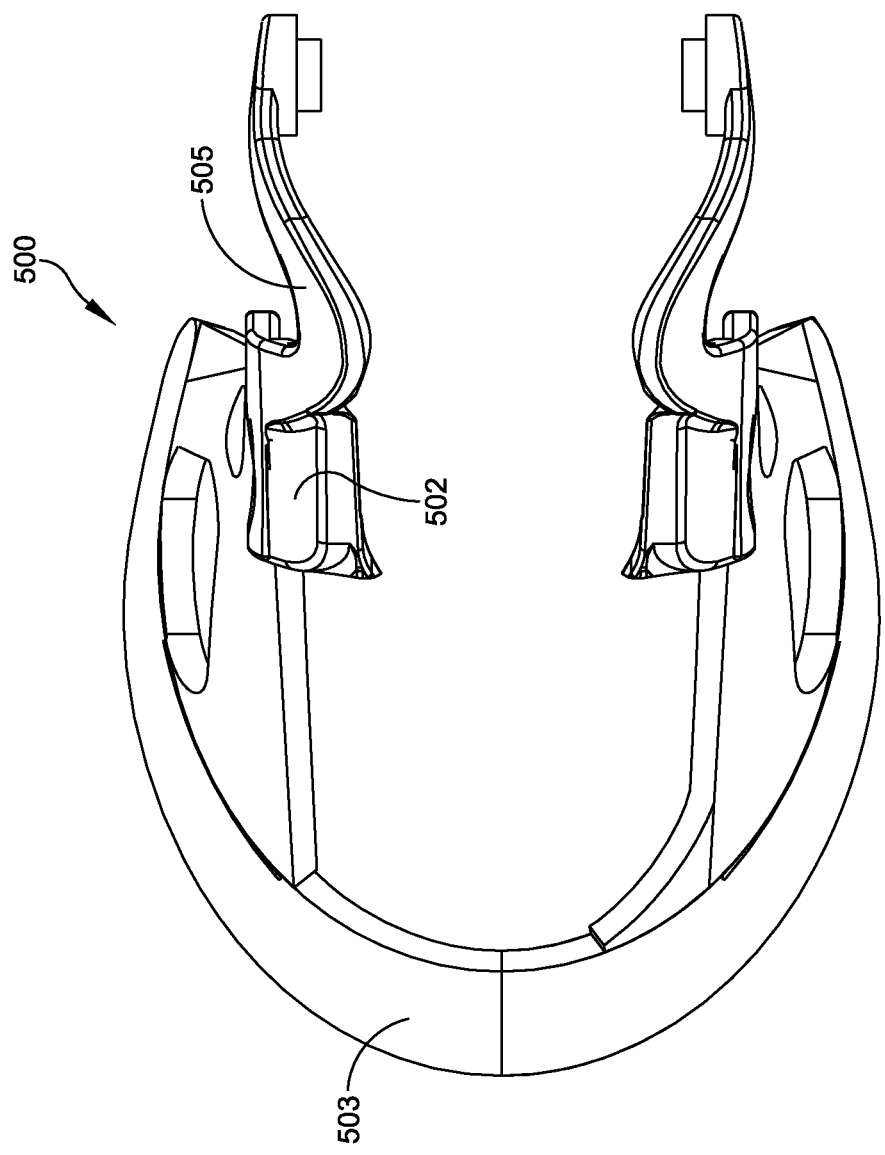
FIG. 10 is a top view of the portion of the prosthetic thumb assembly of FIG. 5.
Figure 11:
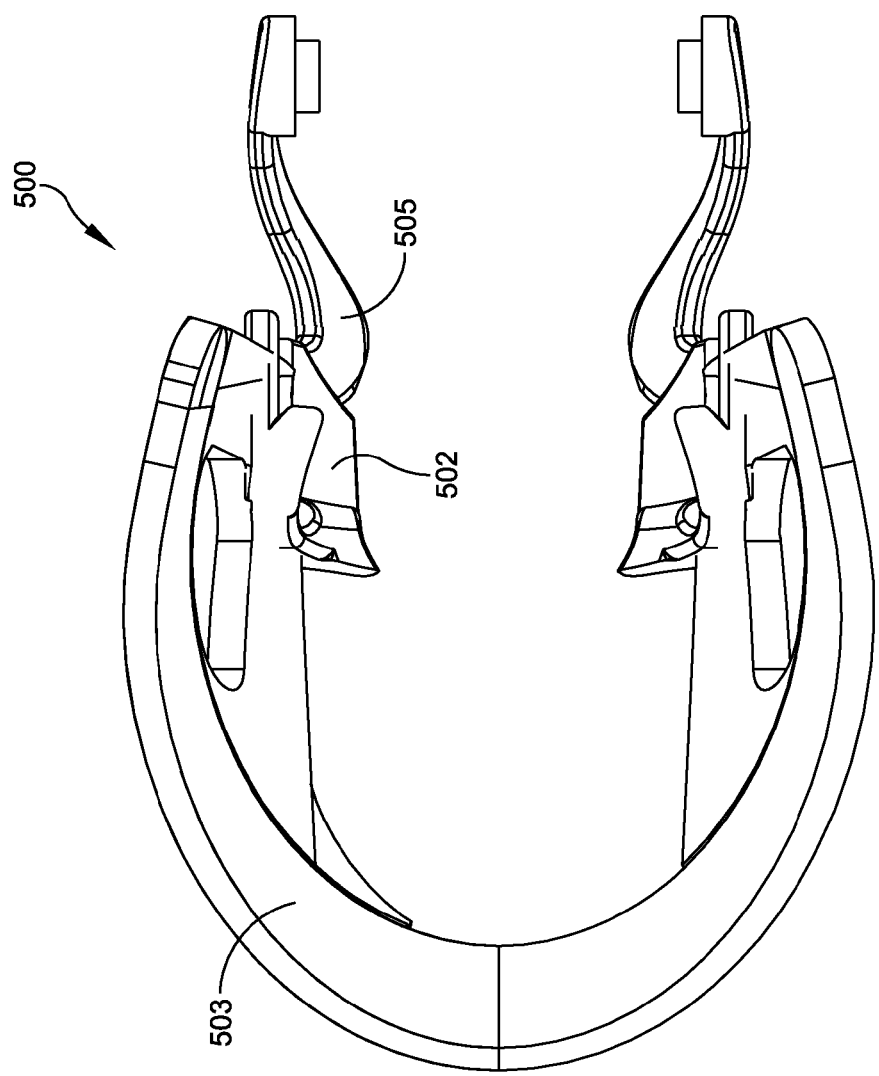
FIG. 11 is a bottom view of the portion of the prosthetic thumb assembly of FIG. 5.
Figure 12:
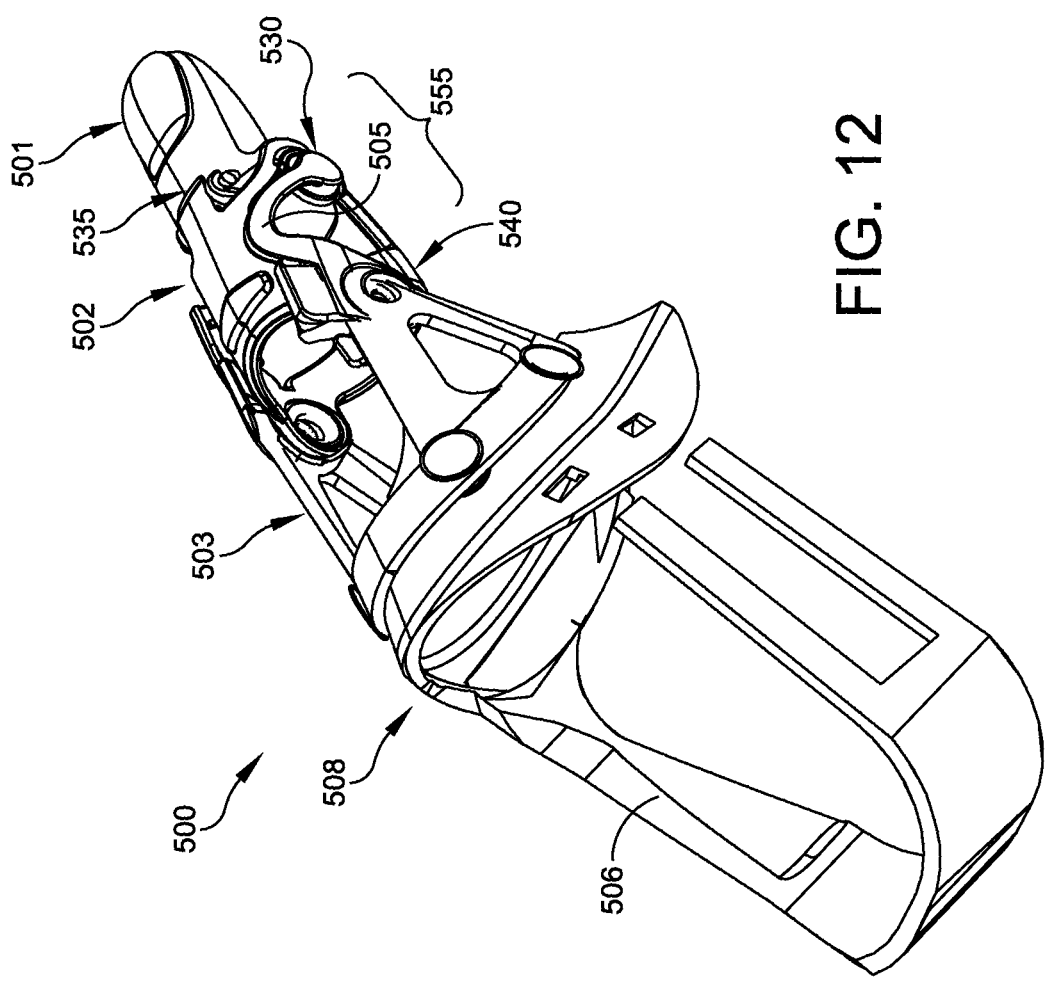
FIG. 12 is a perspective view of an exemplary embodiment of the prosthetic thumb assembly together with the finger tip and the thumb strap.
Figure 13:
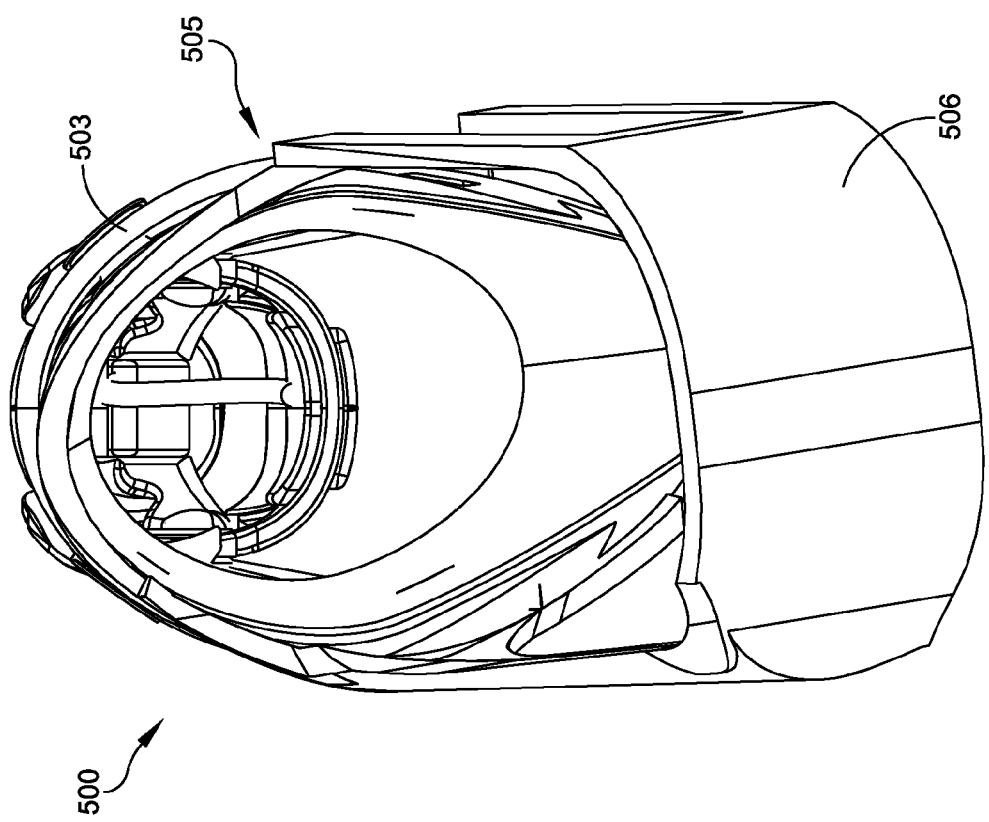
FIG. 13 is a front view of the prosthetic thumb assembly together with the finger tip and the thumb strap.
Figure 14:
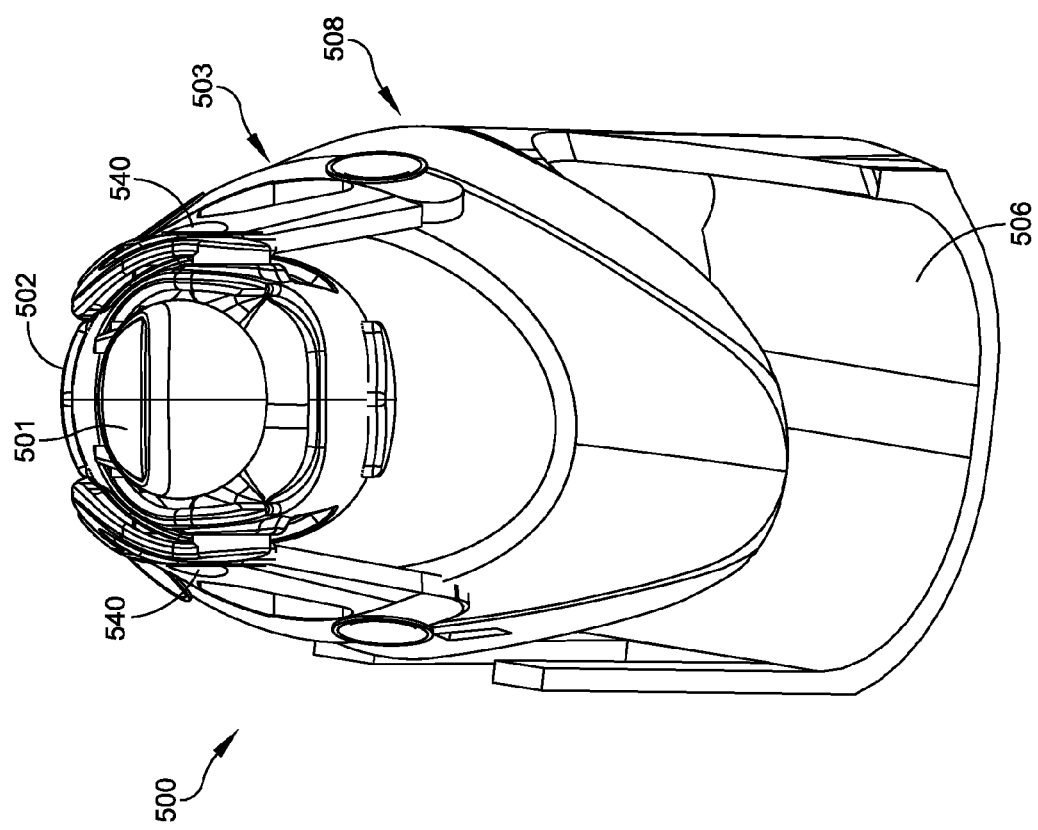
FIG. 14 is a rear view of the prosthetic thumb assembly together with the finger tip and the thumb strap.
Figure 15:
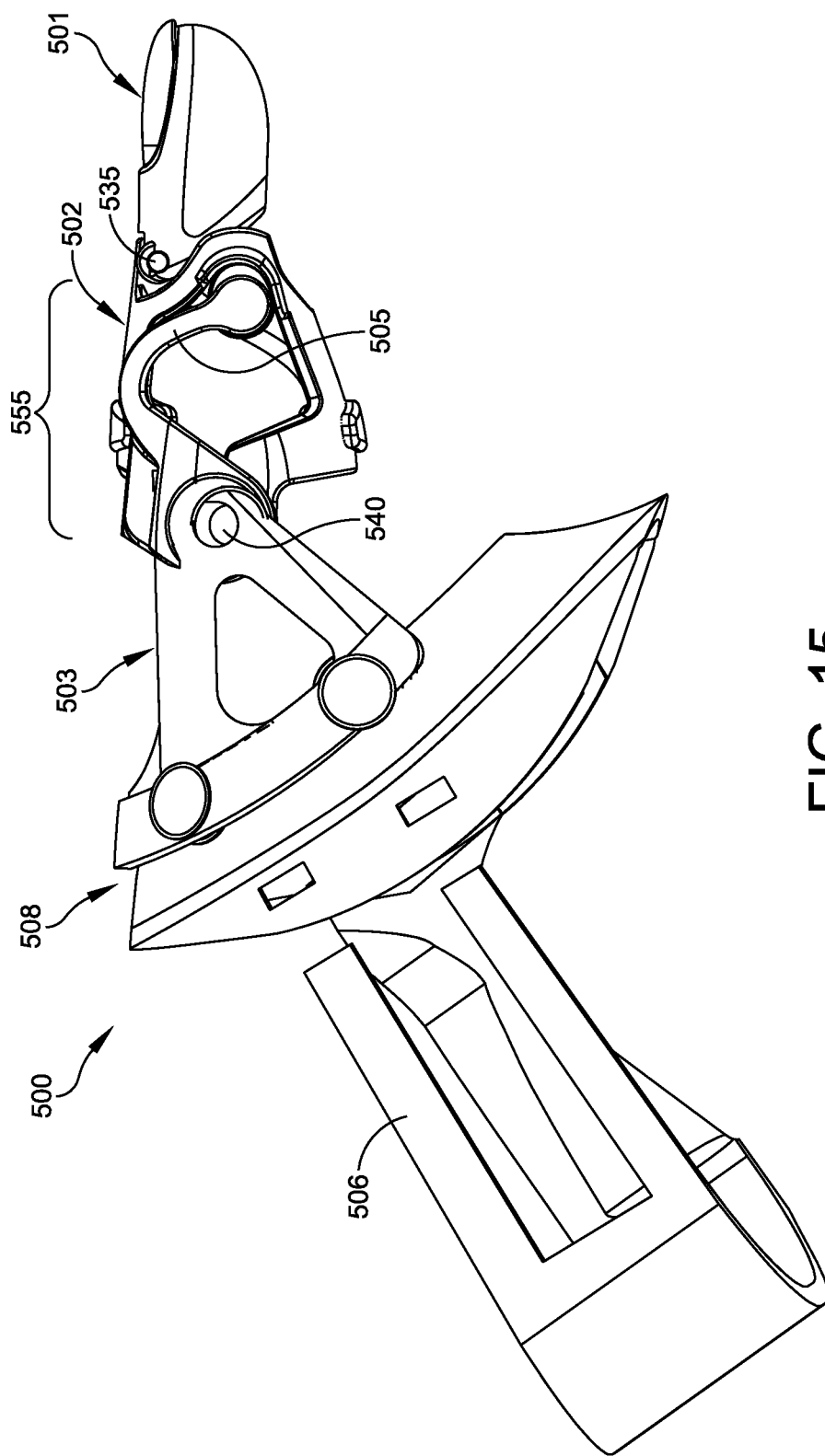
FIG. 15 is a right view of the prosthetic thumb assembly together with the finger tip and the thumb strap.
Figure 16:
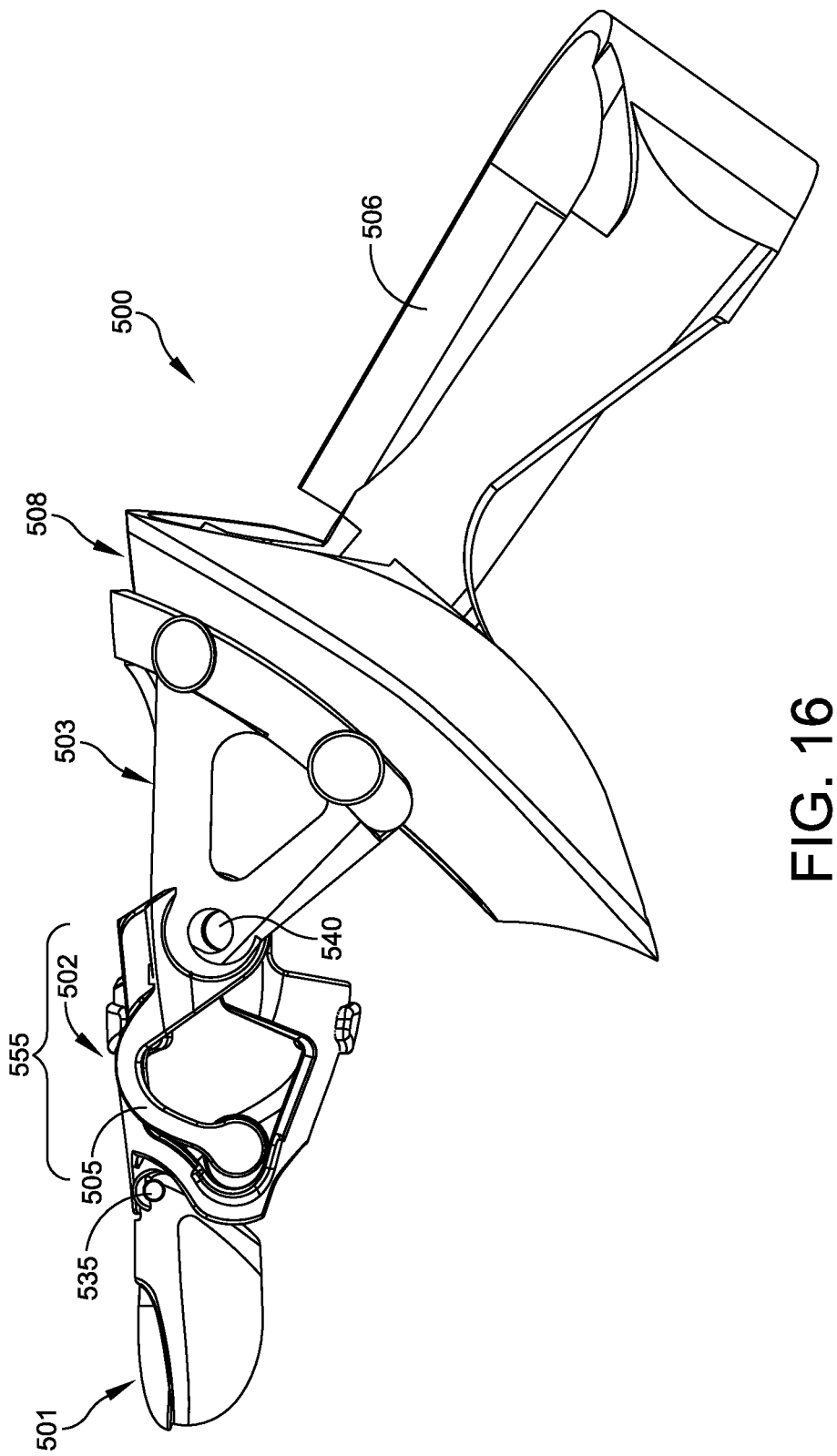
FIG. 16 is a left view of the prosthetic thumb assembly together with the finger tip and the thumb strap.
Figure 17:
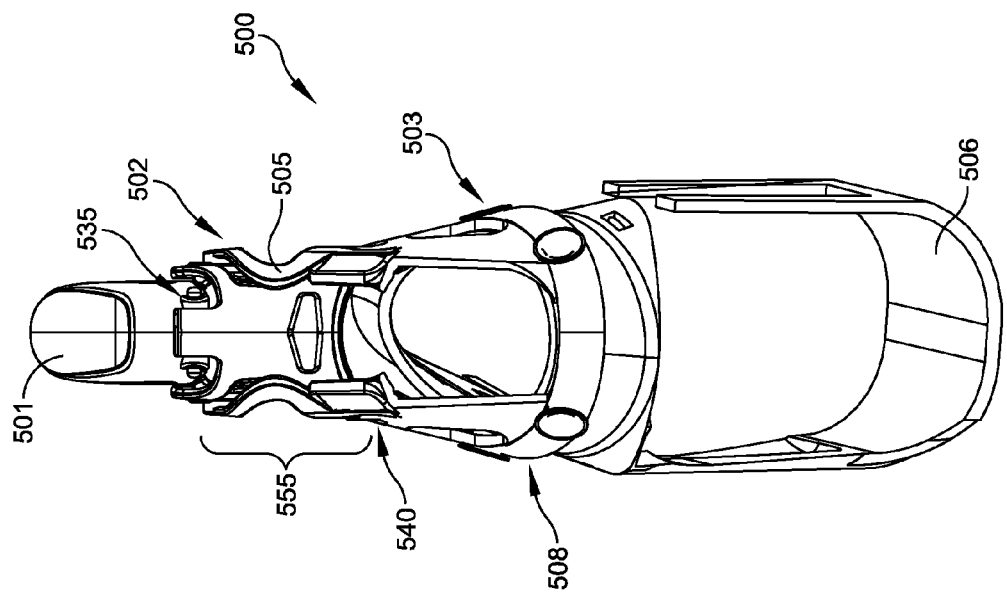
FIG. 17 is a top view of the prosthetic thumb assembly together with the finger tip and the thumb strap.
Figure 18:
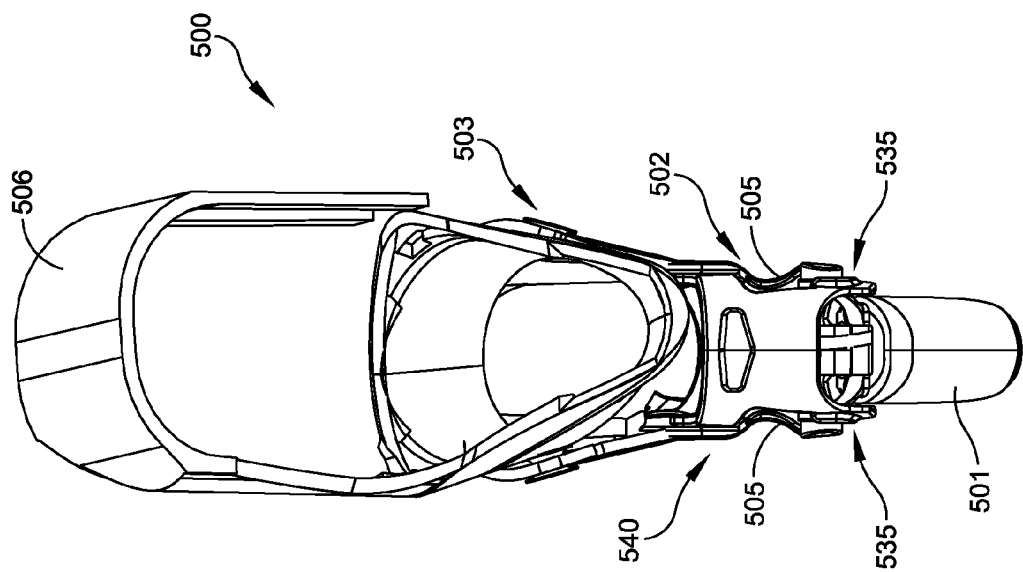
FIG. 18 is a bottom view of the prosthetic thumb assembly together with the fingertip and the thumb strap.
Figure 19:
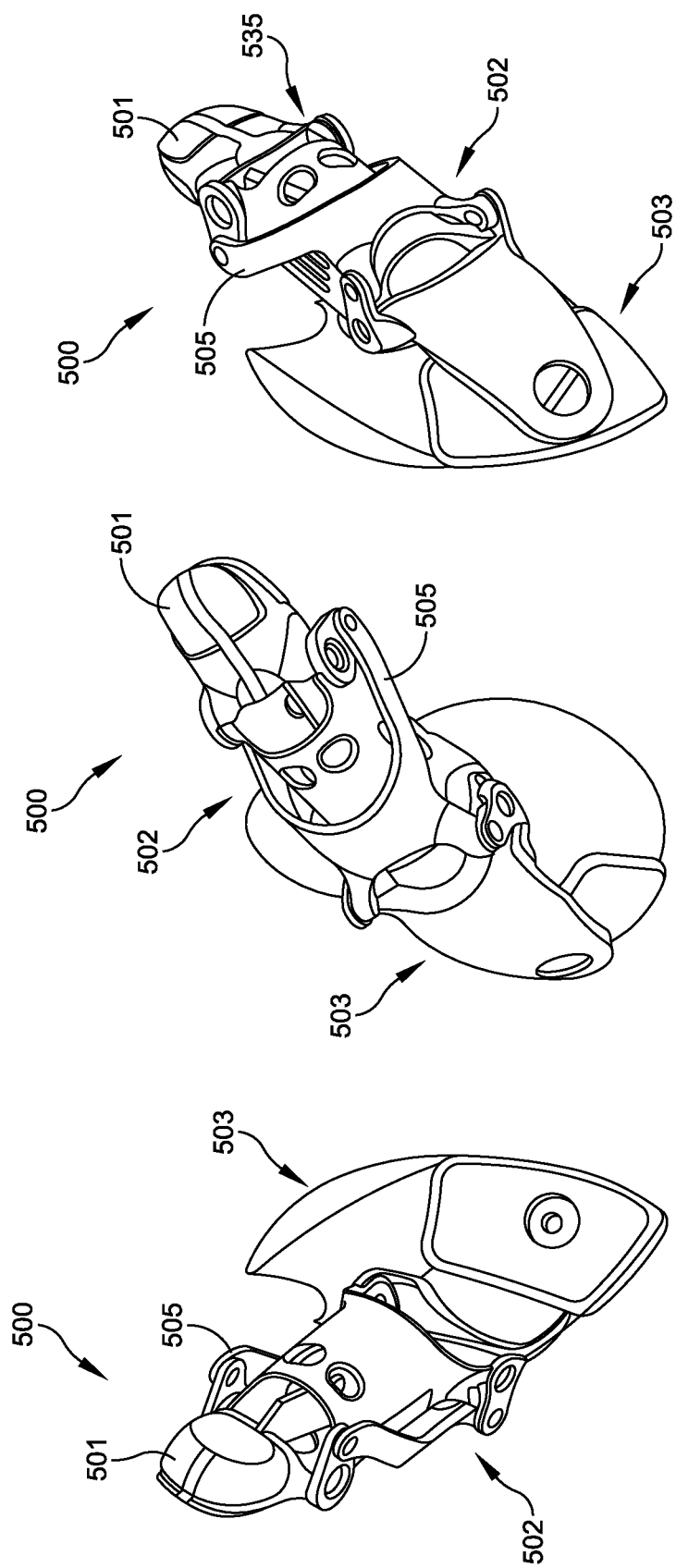
FIG. 19 is an array of an exemplary embodiment of a prosthetic thumb assembly.
Figure 20:
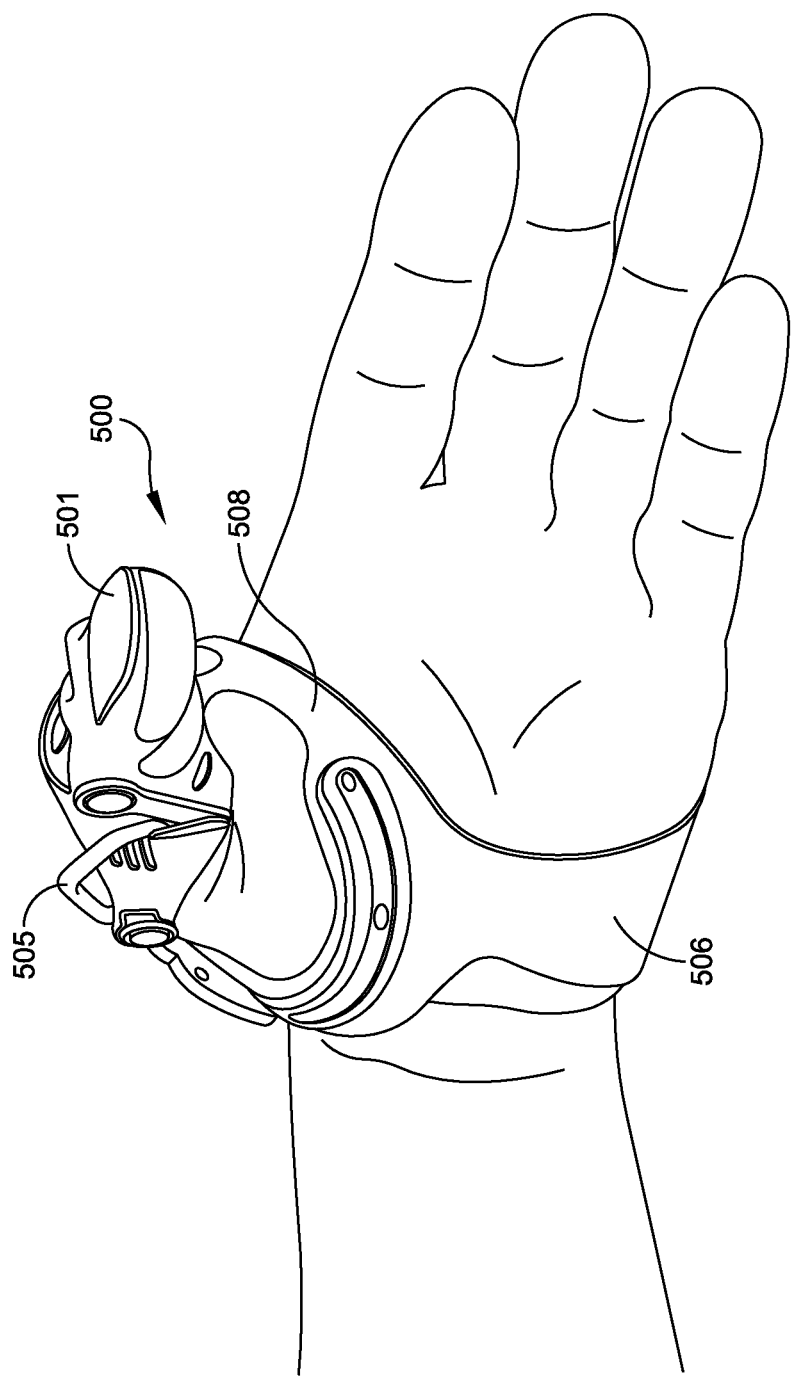
FIG. 20 is a perspective view of a prosthetic thumb assembly disposed on a hand.

In reference to FIG. 4, the articulation cable 9 is connected to the proximal phalanges frame 32 and the lower distal surface. The articulation cable 9 is traversed through the middle phalanges 2 and contributes to the life-like natural movements of the prosthetic finger. The touch screen mechanism 10 comprises a conductive thread 101, and a conductive loop 103. The conductive thread 101 consists of a conductive material such as metal. The conductive loop 103 is the portion of the touch screen mechanism 10 that is used by the user to interact with the touch screen. The conductive loop 103 is made from a conductive material similar to the conductive thread 101. The conductive loop 103 is connected directly to the conductive thread 101. The conductive loop 103 is able to provide the user with the ability to interact with a touch screen at different angles. The distal phalanges 1 includes two holes and two channels able to allow the conductive loop to wrap around the tip of the distal phalanges 1. The two holes are positioned on a first distal corner and a second distal corner. Each of the holes are connected to a respective channel. The conductive loop 103 is traversed through the two channels and connects to the second thread. The conductive loop 103 is left with an exposed segment on the tip of the distal phalanges 1 for interaction with a touch screen. To ensure that the touch screen mechanism 10 fully draws the user's natural body current, the conductive thread 101 can be connected to the finger base brace 313 to ensure contact with the user's flesh. In other embodiments of the present invention, the conductive thread 101 can be connected anywhere on the prosthetic finger as long as it makes contact with a user's flesh.

The present invention provides a comfortable and natural movement for a user with an amputated finger. The design can be individually customized for users with varying amounts of loss on their finger. To further provide better aesthetics, the present invention can be coated with colorings to match the user's skin. The ease of use is another advantage of the present invention. To use the present invention, the user can simply slide the prosthetic finger onto the appropriate finger like a ring. To curl and bend the prosthetic finger, the user can utilize the natural movements of the residual finger that the device is being worn on. The finger segments will articulate using the same cognitive process that was previously utilized for their original finger. Each of the prosthetic fingers can be independently operated. This means the user will be able to perform the activities including full typing, playing a musical instrument, or anything that requires the full dexterity of a hand. The present invention is fully powered by the user's own body. Each component of the prosthetic finger is able to move simply based on the actions of the user's residual finger. The present invention is designed to offer strength in the lowest profile design. As a result, the present invention naturally conforms with the looks of the user's hand.

Medical benefits of the present invention include uses of the device that reduce swelling and increases circulation, supporting the adjacent finger joints. The present device can be made out of Titanium, Stainless Steel, Aluminum, Silicone, Carbon Fiber, Nylon, Plastic, Wood, Rubber, Gold, Silver, Tungsten, Flex Cable, neoprene or any suitable structural material that is non-irritating to human skin. However, in the preferred embodiment of the present invention, the device is made from the material Duraform EX polymer material.

In another embodiment of the present invention, portions of the prosthetic finger can be used for differing conditions of the user. The present invention can be accommodated for fingertips or full fingers. The extended wishbone hinge 321 can be removed so that the prosthetic finger can be used as joint brace. Additionally, using biocompatible materials, the present invention can be applied as an orthopedic implant. Depending on the condition of the user, the present invention can be surgically implanted into the user's fingers. The use of the surgical implantation of the present invention can be applied for users having injuries that have crushed their bones without the ability to heal and be repaired. As a result, the present invention is able to take the place of the user's original bones without the need for amputation.

In various embodiments, the Bio-Mechanical Prosthetic Thumb (BPT) is a specifically designed, self-contained, prosthetic device for partial thumb or thumb-tip amputees. It is an active-function artificial thumb tip. The natural action of the thumb assembly device allows users to regain maximum control of the flexion and extension movements of a thumb tip. It is designed to bend the prosthetic thumb tip in a realistic, natural manner.

In exemplary embodiments, the BPT is a realistic tip, attached to a cap, which fits over the user's remaining thumb. The cap is attached to a ring providing stability during application and use. The three pieces have jointed or flexible connections supporting the smooth, natural turning or pivoting of the device.

In some embodiments, each BPT device is a custom designed and individually fitted prosthetic. The components may include a tip (distal phalanges); a cap (proximal phalanges); a ring worn on the metacarpals region and the ring is attached to a proximal phalanges strap, that wraps around the palm and wraps around to the back of the hand and then loops through two slots that is then anchored in place (e.g., connected with hook-and-loop material); tendon attached to ring; and connectors. The BPT is made of any suitable structural material that is non-irritating to human skin, allowing the user to operate the prosthetic with comfort and confidence In an embodiment, one end of a tendon or cable or housing portion may be attached to a ring, including with a stamped eye and screw. A tendon or cable or housing is routed over and down through a cap and is attached to the bottom or the inside of the tip, a lightweight E/Z connector, with a screw and washer to secure the connector. When the user bends his or her finger or fingers, the device will bend the tip and move in a natural motion.

Features and User benefits of the present invention include but are not limited to the following:

Comfortable and natural movement and use. The design is based on amount of loss, number of joints to be replaced and other personal characteristics, including skin tone/color.

The user slides the BPT device onto the appropriate finger like a ring, and bends the device using the natural movement of the remaining thumb. The thumb segments will articulate using the same cognitive process previously used to articulate their thumb.

Everyone's individual uniqueness dictates the function and performance expected from their hands. Whether you are at work or play, independent control of each device is individually designed and fitted. The BPT is a custom fit device designed to fit about the user's residual thumb, while allowing the necessary activities of today's lifestyles. An active-function artificial finger assembly is provided in a self-contained device. The BPT allows the user to regain control of the articulation of the device simply by moving his or her thumb. Benefits will include typing; playing a musical instrument or anything that requires the full dexterity of a hand.

Because the device is body powered, there is no need for external power supplies. The components articulate simply by moving the residual thumb when available or an opposing thumb when needed.

The components of the BPT have been designed to not only look realistic during articulation, but to also bend a metal or silicone thumb tip in a realistic manner as well. The cable of the device when articulated, gently forces the thumb tip to also bend in a natural manner.

The device has been designed to offer strength while providing a low profile design.

Medical benefits of the present invention include uses of the device that reduce swelling and increases circulation, supporting the adjacent finger joints.

The present device can be made out of Titanium, Stainless Steel, Aluminum, Silicone, Carbon Fiber, Nylon, Plastic, Wood, Rubber, Gold, Silver, Tungsten, Flex Cable, neoprene or any suitable structural material that is non-irritating to human skin.

The thumb works just like the partial finger, only the patient is wearing a thumb strap to keep the thumb partial finger in place. The thumb strap may be the same or similar to the strap of a full finger prosthetic device described in a co-pending patent application. With the thumb strap, it allows the patient to even wear the full finger design.

Referring now to FIGS. 5-20, and in various embodiments, there is shown a prosthetic thumb assembly 500. In an embodiment, the prosthetic thumb assembly 500 may include a distal phalanges 501. A proximal phalanges 502, (which may be referred to as a cage) may be in operable connection with distal phalanges 501. This operable connection may include, but is not limited to, a hinge component. A thumb strap ring 503 (which may also be referred to as a ring or an index ring) may be in operable connection with the proximal phalanges 502. A proximal phalanges yoke 505 may be in operable connection with the thumb strap ring 503. An anchoring portion 508 (including, but not limited to a thumb strap 506) may be in the operable connection with the thumb strap ring 503.

In one embodiment, the ring 503 may be placed about the thumb of the user. With the prosthetic thumb assembly 500 in an extended position, similar to the partial finger design, the proximal phalanges yoke 505 is configured to pull on the cage 502 and force the original mechanics of the partial finger device portion to actuate when the user bends the metacarpal joint in his or her hand. In various embodiments, ring 503 may be held in place using thumb strap 506. This thumb strap 506 may be used with a thumb prosthetic device as well as the full finger assembly 500.

In one embodiment, the anchoring portion 508 may include a thumb strap 506.

The operable connection of the proximal phalanges 502 with the distal phalanges 501 may include a pair of distal hinges 530 and a proximal pulling hinge 535. The operable connection of the ring 503 with the proximal phalanges 502 may include a pair of proximal hinges 540.

In another embodiment, there is disclosed a prosthetic full finger assembly 500 with distal phalanges 501 having an operable connection 530 at its proximal end. The ring 503 may have an operable connection adjacent a distal end thereof and an anchor adjacent a proximal end thereof. Articulation components 555 may be configured between the distal phalanges 501 and the ring 503.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A prosthetic thumb assembly comprising:
   a distal phalanges;
   a proximal phalanges having a proximal end and a distal end, the distal end of the proximal phalanges having a direct pivoting connection with the distal phalanges;
   a thumb strap ring having a direct pivoting connection with the proximal end of the proximal phalanges;
   a proximal phalanges yoke having a proximal end and a distal end, the distal end of the proximal phalanges yoke having a direct pivoting connection with the proximal phalanges, and the proximal end of the proximal phalanges yoke having a direct pivoting connection with the thumb strap ring; and
   an anchoring portion having an operable connection with the thumb strap ring;
   wherein when the prosthetic thumb assembly is in use, the distal phalanges, the proximal phalanges, the thumb strap ring, and the proximal phalanges yoke fit concentrically about a user's residual thumb.

2. The assembly of claim 1 wherein the anchoring portion includes a thumb strap.

3. The assembly of claim 1, wherein the direct pivoting connection of the distal end of the proximal phalanges with the distal phalanges includes a pair of distal hinges and a proximal pulling hinge.

4. The assembly of claim 1, wherein the direct pivoting connection of the thumb strap ring with the proximal end of the proximal phalanges includes a pair of proximal hinges.

5. The assembly of claim 1, wherein the direct pivoting connection between the thumb strap ring and the proximal end of the proximal phalanges yoke is a hinge adjacent a distal end of the thumb strap ring and adjacent the proximal end of the proximal phalanges yoke.

6. A prosthetic thumb assembly, comprising:
a distal phalanges;
a thumb strap ring;
a proximal phalanges disposed between the distal phalanges and the thumb strap ring;
a proximal phalanges yoke having a proximal end and a distal end, the distal end having a direct pivoting connection with the distal phalanges and the proximal Phalanges, the proximal end having a direct pivoting connection with the thumb strap ring and the proximal phalanges; and
an anchoring portion having an operable connection with the thumb strap ring.

7. The assembly of claim 6, wherein the anchoring portion includes a thumb strap.

8. The assembly of claim 6, wherein when the prosthetic thumb assembly is in use, the distal phalanges, the proximal phalanges, the thumb strap ring, and the proximal phalanges yoke fit concentrically about a user's residual thumb.

9. The assembly of claim 6, further comprising a direct pivoting connection between the proximal phalanges and the distal phalanges.

10. The assembly of claim 9, wherein the direct pivoting connection between the proximal phalanges and the distal phalanges includes a pair of distal hinges and a proximal pulling hinge.

11. The assembly of claim 6, further comprising a direct pivoting connection between the thumb strap ring and the proximal phalanges.

12. The assembly of claim 11, wherein the direct pivoting connection between the thumb strap ring and the proximal phalanges includes a pair of proximal hinges.

\* \* \* \* \*